United States Patent [19]

Levy et al.

[11] 4,256,100
[45] Mar. 17, 1981

[54] FLOW CONTROL EQUIPMENT

[75] Inventors: Donald Levy, River Vale, N.J.; Tibor Rusz, Pittsfield, Mass.

[73] Assignee: Rule Medical Instruments, Inc., Pittsfield, Mass.

[21] Appl. No.: 11,636

[22] Filed: Feb. 12, 1979

[51] Int. Cl.³ .............................................. A61M 16/00
[52] U.S. Cl. ......................... 128/204.21; 128/205.24; 128/205.15; 137/599
[58] Field of Search ............... 128/145.5, 145.6, 145.8, 128/188, 205.24, 204.21, 204.23, 204.24, 205.15, 205.16; 137/599, 487.5

[56] References Cited

U.S. PATENT DOCUMENTS

| | | | |
|---|---|---|---|
| 3,033,195 | 5/1962 | Gilroy et al. | 128/145.6 |
| 3,072,146 | 1/1963 | Gizeski | 137/599 |
| 3,726,296 | 4/1973 | Friedland et al. | 137/599 |
| 3,741,208 | 6/1973 | Jonsson et al. | 128/145.6 |
| 3,827,457 | 8/1974 | Vutz et al. | 137/599 |
| 3,840,006 | 10/1974 | Buck et al. | 128/145.8 |
| 3,905,363 | 9/1975 | Dudley | 128/145.8 |
| 3,921,628 | 11/1975 | Smythe et al. | 128/145.6 |
| 3,942,553 | 3/1976 | Gallatin | 137/599 |
| 4,001,700 | 1/1977 | Cook et al. | 128/145.5 |
| 4,036,221 | 7/1977 | Hillsman et al. | 128/145.6 |
| 4,134,423 | 1/1979 | Mayer | 137/487.5 |
| 4,170,245 | 10/1979 | Haley | 137/487.5 |

FOREIGN PATENT DOCUMENTS

| | | | |
|---|---|---|---|
| 2745528 | 4/1978 | Fed. Rep. of Germany | 128/204.21 |
| 2851490 | 5/1979 | Fed. Rep. of Germany | 128/204.21 |
| 2910094 | 9/1979 | Fed. Rep. of Germany | 128/204.21 |

*Primary Examiner*—Henry J. Recla
*Attorney, Agent, or Firm*—Frederick W. Padden

[57] ABSTRACT

An anesthesia ventilator is disclosed for controlling the flow of air and/or oxygen through a plurality of binary weighted valves from a fluid regulator source to a bellows assembly. Directly-set minute volume, breath rate and inspiration to expiration ratio controls operate electronic circuitry which adjusts the magnitude of the flow, the tidal volume and the inhalation to exhalation times. The circuitry includes alarm detecting devices for alerting personnel that a patient should be ventilated manually, that a patient is disconnected from the instrument, that control settings exceed specifications for the instrument, that undesired low gas pressure exists and that actual inspiration to expiration is less than that of the control setting. Flow and tidal volume limiting apparatus is provided, together with sigh circuitry and devices for correcting for altitude and gas parameters.

30 Claims, 11 Drawing Figures

| FIG. 7 | FIG. 8 |
| --- | --- |
| FIG. 9 | FIG. 10 |

FLOW CONTROL EQUIPMENT

TECHNICAL FIELD

This invention relates to flow control equipment and particularly to facilities suitable for use in anesthesia equipment for automatically controlling the flow, volume, rate and inspiration to expiration ratios of air and/or gas delivered to a patient.

BACKGROUND ART

Physicians and other skilled personnel customarily specify the ventilation of a patient based on physiological parameters. Typically, the specified ventilation is in terms of tidal volume, minute volume, breath rates, and inhalation to exhalation ratios.

A persistent problem in this field has been that heretofore time consuming and complicated human procedures have been required for adjusting prior art ventilators, such as anesthesia respirators, to deliver the required ventilation. The procedure generally involves the use of a watch for timing pneumatic equipment operations and determining the number of breaths per minute, the minute volumes and inhalation-exhalation times. While performing these functions, the timing person is required to adjust a multitude of respirator controls until the desired ventilation is achieved. In doing so, the human being, rather than the equipment, controls when the appropriate minute volume, tidal volume, breath rate, and inspiration-expiration ratios are achieved.

In view of the foregoing, a need has heretofore existed for flow control facilities which eliminates the prior art manual timing and adjustment procedures and automatically regulates the flow by the direct setting of minute volume, breath rate and inspiration-expiration controls.

DISCLOSURE OF THE INVENTION

The foregoing problem is solved and a technical advance is achieved in accordance with a preferred illustrative embodiment of this invention comprising flow control equipment which automatically regulates the delivery of prescribed tidal volumes of fluid flow from a source to a utilization means under control of directly-set minute volume, breath rate, and inspiration to expiration ratio control dials. The control equipment includes a plurality of valves for switching the flow on and off, a flow circuit for operating the valves to determine the magnitude of the flow delivered, and a tidal volume circuit which cooperates with the flow circuit for controlling the operated time of the valves so that a prescribed tidal volume of the fluid is delivered from the source to the utilization means. A breath rate circuit is furnished for establishing the total time for inspiration and expiration.

The flow and tidal volume circuits are automatically driven by an internal clock and a binary counter arrangement. Therefore, no manual timing is needed. The only functional adjustments required to be made are the three control dials for minute volume, breath rate and inspiration-expiration ratio.

A sigh circuit is provided which is activated by the breath rate circuit after a defined number of breaths for causing a sigh flow that illustratively is an inspiration tidal volume increase to 150% of normal and an expiration time increase to 150% of normal.

Visual and audible alarms are included to indicate equipment malfunction, the nondelivery of set volumes, transient cessations of breathing (apnea), and incorrect settings of the minute volume, rate and inspiration-expiration dials.

Check circuitry is integrated into the flow control equipment to limit the maximum fluid flow and tidal volume of that flow. Circuitry is also included for correcting altitude and driving gas variations in different geographical areas.

In the illustrative embodiment, the flow control equipment is equipped with five valves. Each of the valves is operable for delivering a different mangitude of fluid flow from the source to the utilization means. The valves are operable in different combinations to deliver desired magnitudes of fluid flow. Illustratively, the five valves respectively deliver 2, 4, 8, 16 and 32 liters per minute for a total of 62 liters per minute when all five valves are operated.

The desired magnitude of flow is controlled by the setting of the minute volume and inspiration-expiration control dial settings. The latter control a scaler and multiplier which perform the arithmetic for generating a flow voltage. A comparator examines the flow voltage against a control signal generated by a digital to analog converter in response to a binary count generated by the clock and counter. When the control signal exceeds the flow voltage, the comparator activates a latch which supplies appropriate binary count signals from the counter to respective ones of five conductors 2, 4, 8, 16 and 32 for operating via five "OR" and "AND" gates the respective ones of the 2, 4, 8, 16 and 32 liters per minute valves for starting an inspiration interval.

The "OR" gates form part of a check circuit which limits the flow illustratively to 62 liters per minute whenever the minute volume and inspiration-expiration control dials are set incorrectly for a resultant delivery of abnormally high flows. This check circuit includes a comparator which compares the flow voltage with a reference voltage (maximum flow) and forces the operation of all five valves via the "OR" gates when the flow voltage is greater than the reference voltage.

The "AND" gates are serially inserted between the "OR" gates and the valves and are normally enabled by the tidal volume circuit during the entire inspiration interval. The gates are disabled to release, or close, the valves for terminating the inspiration interval when a prescribed tidal volume has been delivered from the fluid source through the valves to the utilization means.

The binary count signals 2, 4, 8, 16 and 32 furnished by the "AND" gate outputs for operating the valves are advantageously supplied to the tidal volume circuit for precisely controlling the tidal volume delivered through the valves. A digital to analog converter in the tidal volume circuit converts these count signals by scaling action into accurate representations of the actual flow delivered by each of the five valves such that any inaccuracies caused by valve adjustments or restrictions are compensated for. The converted signals are then integrated and the resultant output signal forms one tidal volume input to a tidal volume comparator. Another tidal volume input to that comparator is derived by a signal processing circuit driven by the scaler and multiplier in accordance with the minute volume and rate dial settings, by the clock and counter, and by the altitude and gas correction circuitry.

The scaler and multiplier supplies a breath rate voltage which is integrated and then matched in another comparator against a minute volume voltage supplied by the scaler and multiplier. When the two voltages are equal, the comparator activates another latch via an OR gate to extend to a digital to analog converter a binary count derived from predetermined outputs of the counter. The converter sums the received binary count signals and passes the summed signal through the altitude and driving gas correction circuitry to the tidal volume comparator. The corrected signal thus supplied to the comparator represents the desired tidal volume specified by the settings of the minute volume and rate control dials.

When the corrected signal equals the voltage at the integrator input to the comparator, the desired tidal volume has actually been delivered through the valves. Accordingly, the comparator disables the "AND" gates in the flow circuit to terminate the inspiration interval by effecting the release, or closing, of the valves and thereby commencing the expiration interval.

The expiration interval is terminated under control of the rate circuit. It comprises an integrator which integrates a rate voltage received from the scaler and multiplier in accordance with the breath rate control setting. The integrated voltage is supplied to a comparator which compares it against a reference voltage. When the two voltages are equal, the comparator terminates the expiration interval by applying a reset, or recycling, signal to the rate integrator and the flow integrator in the tidal volume circuit. At the same time, the reset signal advances by one the count of the sigh counter circuit. Upon the resetting of the flow integrator, the tidal volume comparator is operative to fully enable the "AND" gates in the flow circuit so that the appropriate valves are again operated and another inspiration interval is begun.

The flow control equipment is further equipped with a tidal volume limiting circuit to limit the maximum tidal volume in case of incorrect settings of the minute volume and rate control dials. The limiting circuit includes an integrator which operates in synchronism with the rate voltage integrator in the determination of tidal volume. The limit integrator integrates a reference voltage. The output of that integrator is compared in a comparator with the reference voltage and, when the two are equal, the comparator activates the tidal volume latch to fix the tidal volume count at its output to that of the binary counter. The latch output is thereafter used to control the tidal volume comparator as priorly explained.

A reset arrangement driven by the clocked counter is integrated into the flow control equipment for automatically recycling the tidal volume and rate integrating circuitry at periodically recurring intervals. This promotes accuracy in tidal volume delivery and at the desired rate. It also enables the equipment to respond to resetting of minute volume, breath rate and inspiration-expiration dials.

In view of the foregoing, the flow control equipment comprises a plurality of valves each of which is individually operable to deliver a predetermined fluid flow from a source to a utilization means, and means responsive to a receipt of prescribed minute volume, breath rate, and inspiration-expiration ratios signals for controlling the operations of said valves to deliver a fixed tidal volume of said fluid from said source to said utilization means.

DRAWING DESCRIPTION

The foregoing and other features of the specific illustrative embodiment are more fully understood from a reading of the following description with reference to the drawing in which.

DETAILED DESCRIPTION

Figures 1, 11:
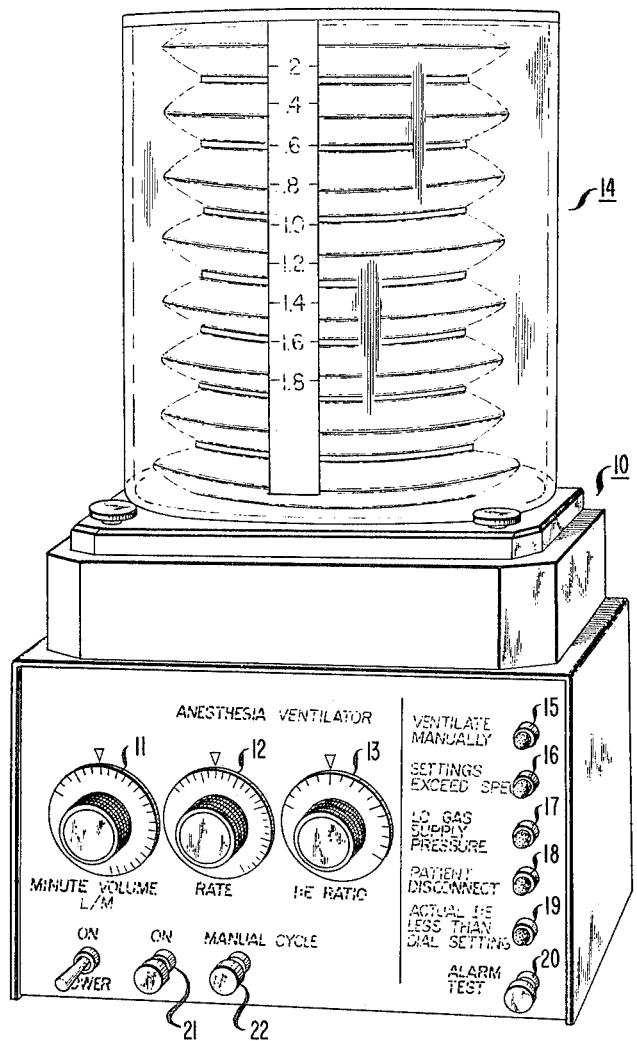
FIG. 1 shows an overall view of an exemplary anesthesia ventilator utilizing the flow control equipment.
FIG. 11 shows the functional alignment of FIGS. 7-10.

As depicted in FIG. 1, a ventilator instrument 10 is illustratively used as an anesthesia ventilator. It is equipped with three front panel dials 11, 12 and 13 which form part of the flow control circuitry. These dials are directly set according to physiological parameters of a patient to deliver prescribed oxygen and/or gas flow, volume, breath rate and inspiration-expiration ratio to the patient via a bellows assembly 14. Instrument 10 is also equipped with visual alarms 15, 16, 17, 18 and 19 for respectively indicating instruments malfunctions requiring manual ventilation, the settings exceed specifications, low gas supply pressure, patient disconnected, and the delivered inspiration-expiration rate less than settings. Pushbutton switch arrangement 20 is provided to test the operability of alarms 15-19. The functioning of a sigh circuit in instrument 10 is indicated by a front panel switch 21. A cycle initiating switch 22 is furnished in instrument 10 for manually starting an inspiration cycle.

Figure 2:
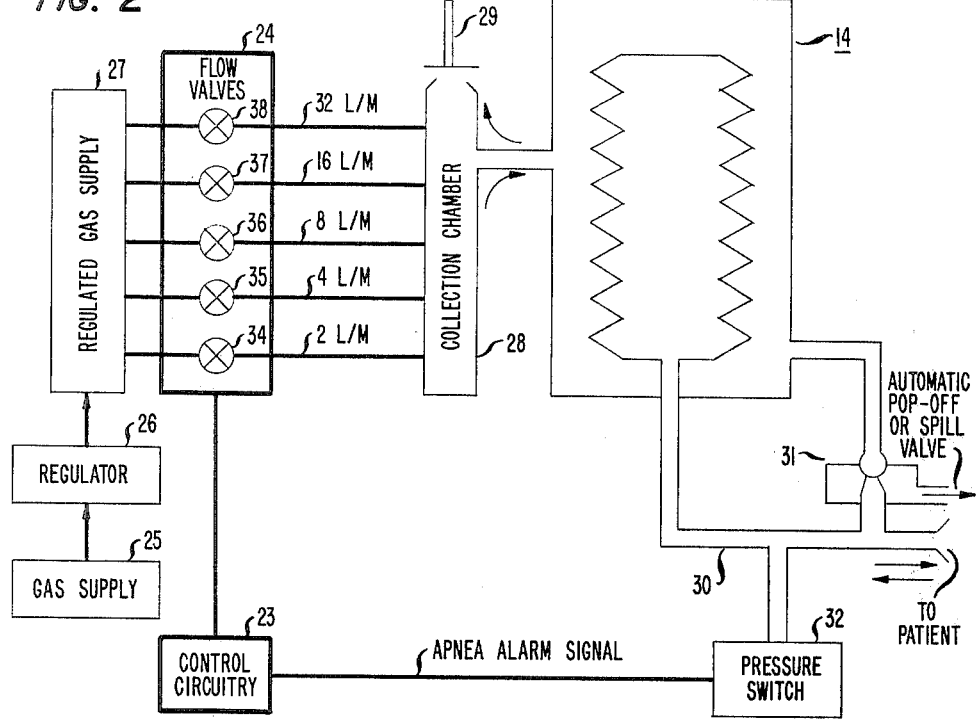
FIG. 2 illustrates, in block diagram form, the interrelationship of the flow, tidal volume, breath rate and inspiration to expiration ratio control circuitry and flow valves with conventional anesthesia facilities.

FIG. 2 shows the functional interrelationship of the exemplary flow, tidal volume, breath rate and inspiration-expiration ratio control circuitry 23 and flow valve assembly 24 with a known bellows assembly 14. The control circuitry 23 switches a plurality of the flow valves in assembly 24 to control the inhalation delivery of the prescribed oxygen and/or gas flows, volumes at prescribed breath rates and inspiration-expiration ratios to a patient in accord with the setting of dials 11, 12 and 13 of FIG. 1. The inhalation flow is illustratively from a supply 25 through regulator 26, a regulated gas supply device 27, valve assembly 24, a collection chamber 28 equipped with a conventional expiratory valve 29, bellows 14 and a conduit 30 extending to a patient (not shown). A conventional popoff or spill valve 31 functionally exhausts conduit 30. A pressure switch 32 is connected to conduit 30 for furnishing an apnea or patient disconnect signal in response to such a condition existent in that conduit. Patient exhalation is also conveyed through conduit 30 in a known manner.

Mathematical Relationships of Breath Rate, Minute Volume, Tidal Volume, Inspiration, Expiration Ratios and Flows Before proceeding with a detailed description of the structure and operations of the flow control circuitry as depicted in FIGS. 6 and 7-10, it is deemed advisable to define terms and to express the relationship between parameters mathematically.

R = Rate = number of breaths per minute

MV = Minute Volume – number of liters per minute of exchanged oxygen and/or gas

TV = Tidal Volume = the volume of each breath

I = Inspiration Time = the time during which oxygen and/or gas is supplied to the patient lungs E = Expiration Time = the time during which air and/or gas is exhaled from the patient lungs including any end expiratory pause I:E = I:E Ratio – the ratio of inspiration to expiration times. Conventionally expressed as 1:to a number such as 1:1, 1:2 or 1:3, etc.

F = Flow = the actual flow at any given instant and is expressed in liters per minute.

A basic relationship exists between rate, minute volume and tidal volume, namely, Minute Volume = Rate X Tidal Volume or MV = R × TV The average volume or minute volume of flow is equal to the volume of each breath times the number of breaths per minute. Typical ranges of prior art instrumentation are reported as:

R = 10 to 20 breaths per minute
TV = 0.5 to 1 liter per breath
MV = 5 to 10 liters per minute The illustrative embodiment of the anesthesia ventilator 10 ranges are:

R = 6 to 40 breaths per minute
TV = 0.1 to 1.5 liters per breath
MV = 2 to 30 liters per minute
I:E = 1:1 to 1:3

Figure 3:
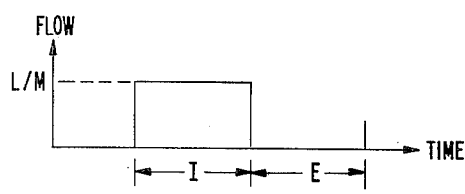
FIGS. 3 and 4 depict illustrative flow, minute volume, inspiration and expiration waveforms with time.

As depicted in FIG. 3, the flow F during inspiration is a steady flow. (During normal spontaneous breathing the flow may or may not be steady.) Inspiration persists for a defined time as does expiration.

Figure 4:
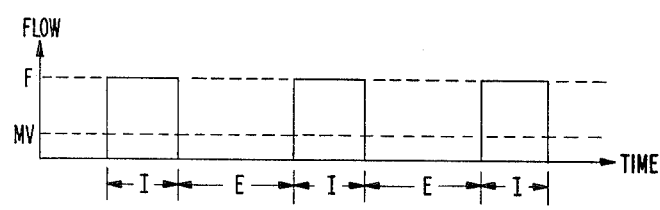

Considering tidal volume, minute volume, rate and I:E ratio for steady breathing, a graph representation is depicted in FIG. 4. F is the flow during inspiration, I is the inspiration time, and E is the exhalation time. The tidal volume F times I, which is the volume of each breath. The minute volume is the volume exchanged in one minute and is the averaged flow expressed in liters per minute. Therefore, $$MV = (F \times I)/(I+E)$$

and $$F = MV(1 + E/I)$$

which is the actual flow during inspiration and is thus independent of rate.

In order to express F in terms of TV, R and I:E;

$$F = MV (1 + E/I)$$

where MV = TV × R yielding by substitution:

$$F = TV \times R(1 + E/I)$$

For the design of the control circuitry in instrument 10, the foregoing mathematical relationships define the following two choices for a dial-in of basic physiological data:

(1) Set MV, R and I:E or
(2) Set TV, R and I:E. TV is useful because the existing respirators are limited generally to the final results of control settings which appear as bellows displacement and are read as tidal volume.

The MV is more fundamental because in order to determine a patient's ventilation with TV, the rate has to be known which finally is MV = R × TV.

Accordingly, the illustrative embodiment as depicted in FIGS. 1 and 6–10 utilizes the MV, R and I:E settings by means of control dials 11, 12 and 13 for MV adjustable from 2 to 30
R adjustable from 6 to 40
I:E adjustable from 1:1 to 1:3

Basic Flow Control System (FIGS. 1, 2 and 3)

The specific exemplary embodiment of the control circuitry utilizes a simple system for performing the arithmetic together with a simple and effective means of controlling the flow.

Fundamentally considering the flow control system, the illustrative embodiment utilizes five valves 34, 35, 36, 37 and 38 as illustrated in FIG. 2. Each such valve is connected to a gas supply 27 which is maintained at a constant pressure by the use of a conventional pressure regulator 26. Each of the valves 34–38 is adjusted so that respectively 2, 4, 8, 16 and 32 liters per minute are deliverable from supply 27 to a collection chamber 28. The binary relationship is not essential, but, as will be explained, it is convenient.

Given specified MV, R and I:E, the quantities of flow delivered by valves 34–38 are determined as follows:

$$F \text{ during } I \text{ time} = MV(1 + E/I)$$

(I+E) time in seconds = 60/R (R in breaths/minute) and yielding from $$I + E = 60/R$$

$$I = 60/R(E/I + 1)$$

and the time for one cycle = 60/R. Thus, by the ventilator instrument valves 34–38 delivering a required flow F for a period I during the total (I+E) time of 60/R, the flow meets all of the MV, rate and I:E control dial 11, 12 and 13 settings (FIG. 1).

In the illustrative embodiment, flow values are selected in binary fashion of 2, 4, 6, 8, 10 ... to 62 liters per minute by means of valves 34–38 of FIG. 2. Accordingly, if, for instance, the prescribed MV setting of dial 11 is 15.5 liters per minute and the I:E setting of dial 13 is 1:1, the required flow F = 15.5 (1+1) = 31 liters per minute. The valves 34–38 controllably provide 30 or 32 liters per minute or an error of one part in 31 or approximately 3% difference from 31. Several solutions to correct the flow error are available as follows:

(1) Use additional valves, such as by adding a "1" valve (not shown), thereby to reduce the error by increasing the resolution;

(2) Allow the MV to be set by dial 11 in increments of two and allow I:E to assume only values of 1:1, 1:2 and 1:3. This would insure that F = MV(1+E/I) is always a multiple of 2. Hence, for flow value settings up to 62 liters per minute, the five valves 34–38 are utilized; and (3) A preferred solution as used in the illustrative embodiment is to calculate TV = MV/R and integrate a derived flow signal until the TV is exactly as desired. This approach keeps the valves 34–38 open a little longer than the calculated I time if the required flow is 31 and the actual flow is 30 and the valve open time would be reduced if the required 31 liters per minute is actually 32 liters per minute.

Figure 6:
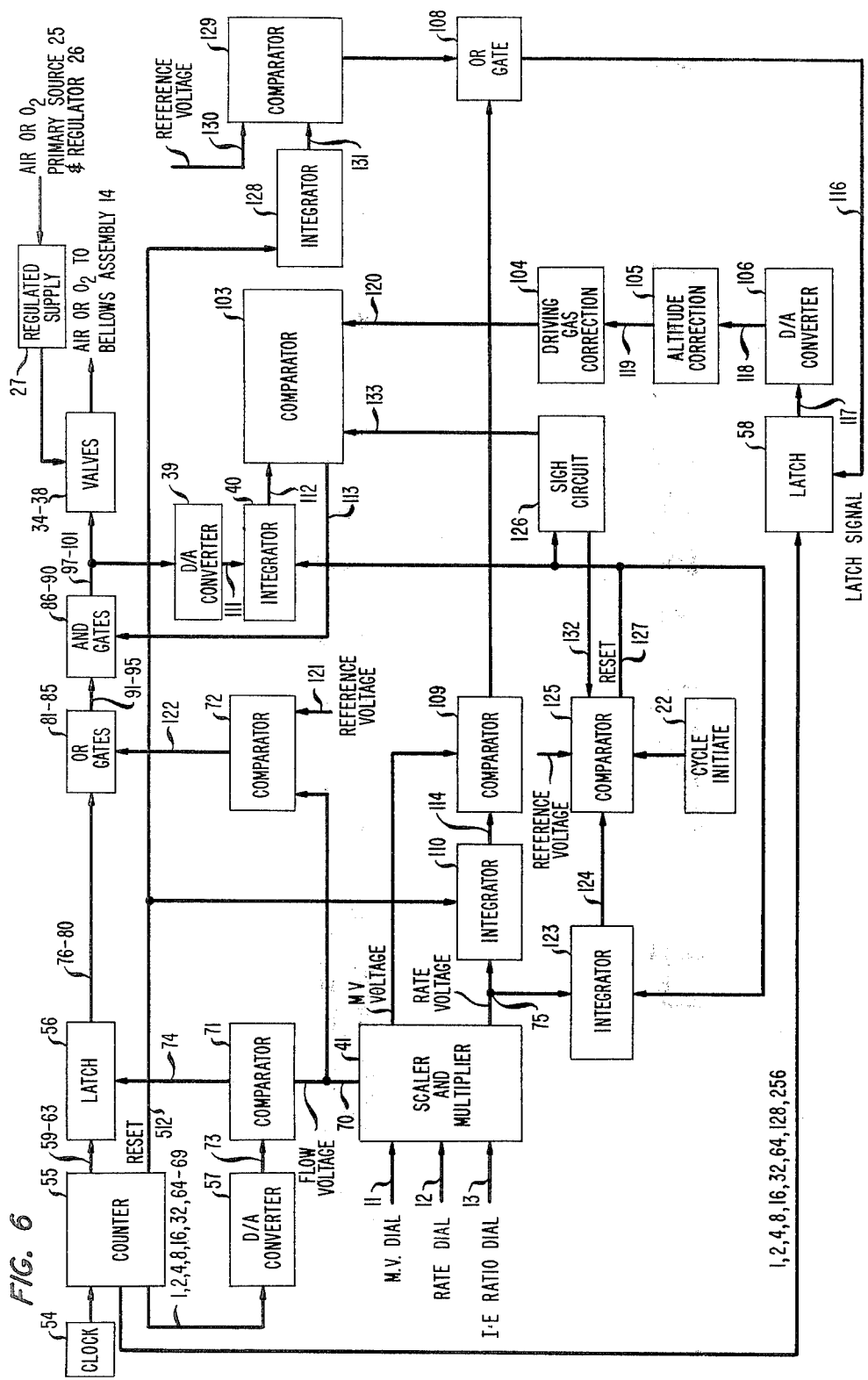
FIG. 6 is a block diagram schematic of the flow, tidal volume and rate control circuits, together with the clock, binary counter, tidal volume and flow limit circuits, sigh circuits, and the scaler and multiplier.

In order to monitor the actual flow delivered by valves 34-38, two methods for flow sensing are available as follows:

(1) Actual flow sensing using known techniques such as a differential pressure device or hot wire system; and (2) A system such as is used in the illustrative embodiment whereby a voltage or current associated with each valve 34-38 is presented to a digital to analog converter 39 and integrator 40 of FIG. 6 when the valves 34-38 are open. The resultant voltage processing by converter 39 and 40 is reflective of the exact value of flow delivered by valves 34-38.

Figure 5:
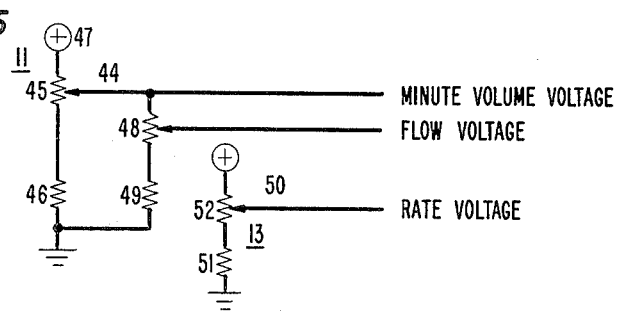
FIG. 5 shows an illustrative minute volume, flow, and breath rate voltage scaler and multiplier.

General Considerations for Designing MV, R and I:E Dials 11, 12 and 13, and Network Scaler and Multiplier 41 of FIGS. 1 and 6 for Deriving Minute Volume, Flow, and Rate Voltages As priorly mentioned, the illustrative embodiment utilizes an MV range of 2 to 30 and an I:E ratio range of 1 to 3. To derive the flow signal voltage $F=MV(1+E/I)$ within these ranges, an exemplary design of MV and I:E dials 11 and 13 and scaler and multiplier 41 of FIG. 6 is shown in FIG. 5. An MV signal voltage is derived at an arm 44 of a linear potentiometer 45 of MV dial 11 which is serially connected with a scaling resistor 46 between ground and a regulated voltage 47. The value of resistor 46 is such that the resistance of potentiometer 45 starts at a factor of 2 rather than zero for the lower MV range of 2. The resistance of potentiometer 45 is linearly adjustable to provide the remaining MV range of 2 to 30 output voltages at arm 44. Voltage 47 is regulated at a value 30 (3+1).

Multiplication of the derived MV voltage at arm 44 times the $(E/E+1)$ for producing a flow signal voltage F is achieved by applying the voltage at arm 44 to a series arrangement of potentiometer 48 and a scaling resistor 49. The value of resistor 49 is such that the resistance of the I:E dial 13 potentiometer 48 starts at 1 rather than zero for the lower I:E range of 1. The value of potentiometer 48 is linearly adjustable to provide the remaining I:E range of 1 to 3. The resultant output voltage at arm 50 of potentiometer 48 is the flow voltage F for the chosen settings of the MV and I:E dials 11 and 13.

Derivation of a rate voltage is accomplished by a series arrangement of a scaling resistor 51 and an R dial 12 potentiometer 52 between ground and a regulated voltage. The value of the resistor 51 is such that the resistance of potentiometer 52 starts at 6 rather than zero for the lower R rate of 6. The value of potentiometer 52 is linearly adjustable to provide the remaining R range of 6 to 40. The resultant output voltage at arm 53 of potentiometer 52 is the rate voltage R for the chosen setting of dial 12.

Control Circuitry (FIG. 6)

This circuitry controls the delivery of prescribed amounts of air or oxygen from the primary source 25 of FIG. 3 through the regulator 26 and regulated supply 27 to a bellows assembly 14 advantageously by means of the five flow valves 34-38. The switched opening and closing of the valves 34-38 to effect the delivery is basically controlled by a clock 54 of FIG. 6 and the settings of the MV dial 11, R dial 12 and I:E dial 13.

Clock 54 recurrently generates output pulses at 1500 Hertz and, in turn, the pulses drive a multistage automatically recycling counter 55. Ten outputs of counter 55 are functionally used to provide five count input signals to a flow signal latch circuit 56 and six count input signals jointly to a flow digital to analog converter 57 and to a tidal volume latch circuit 58. The five count outputs of counter 55 are designated 59-63 and correspond to the counts 2, 4, 8, 16 and 32 required to activate the respective 2, 4, 8, 16 and 32 liters per minute flow delivery valves 34-38. The binary outputs of counter 55 are designated 64-69 and correspond to the counts 1, 2, 4, 8, 16 and 32 utilized for both the flow and tidal volume controls.

Upon the setting of the MV, R and I:E dials 11, 12 and 13 to the prescribed values, a voltage proportional to the flow $F=MV(1+E/I)$ is produced on output 70 of the scaler and multiplier 41. Circuit 41 advantageously comprises operational amplifiers (not shown in FIG. 6) for changing levels (scale factors) and for impedance matching. The flow voltage on output 70 is applied to respective first inputs of comparators 71 and 72.

A second input of comparator 71 is connected to an output 73 of converter 57. The latter sums the voltages on the counter outputs 64-69 with an appropriate scaling factor for each such output for the counts 1, 2, 4, 8, 16 and 32. The scaling factor reflects the magnitude of the count such that, for example, the 32 count contributes 4 times and 8 count and 16 times the 2 count, etc. The voltage on output 73 increases from zero to a maximum of 63 and when it exceeds the flow voltage on output 70, comparator 71 is energized to generate a signal on its output 74 for activating the flow latch 56. The latter comprises five outputs designated 76-80, each of which corresponds to a respective one of its five inputs on 59-63. Upon its activation, latch 56 latches and causes its outputs 76-80 to assume and maintain the then existent binary number count on output leads 59-63. Despite the subsequent changing of the D/A converter 57 voltages at its output 73 under control of the free running and recycling counter 55, the comparator 71 output does not have any effect upon latch 56.

The outputs 76-80 selectively can assume only a value between zero (00000) and 62(11111) in increments of 2. Each of the outputs 76-80 connects to an input of a respective individual one of five OR gates 81-85, the output of which, in turn, is connected to an input of a respective individual one of five AND gates 86-90. The five outputs of gates 81-85 are designated 91-95. The output of each of the gates 86-90 is connected to an individual one of the flow valves 34-38 and to an individual one of five inputs of a D/A converter 39. The outputs of gates 86-90 are designated 97-101.

"OR" gates 81-85 function to pass the binary count signals 2, 4, 8, 16 and 32 from the outputs 76-80 of latch 56 via outputs 91-95 to respective inputs of "AND" gates 86-90 while isolating those signals from override control signals generatable by comparator 72 as hereinafter explained. The latter gates are fully enabled to pass the received binary count signals to the appropriate ones of the valves 34-38 advantageously under control of flow compensating control signals as hereinafter explained.

To facilitate an understanding of the flow control circuitry, a description of the generation of the flow compensating control signals is deferred and it is assumed that the "AND" gates 86-90 are enabled and pass the appropriate then existing binary count signals 2, 4, 8, 16 and 32 from latch 56 via gates 81-85. The passed signals accordingly activate the appropriate one(s) of the valves 34-38.

The valves are normally closed two-way devices. The valves are connected so that the 2 liters per minute valve 34 is connected to the "2" count line, the 4 liters per minute valve 35 is connected to the "4" count line and so forth. All of the foregoing flow control circuit actions serve to generate a flow in the range from zero to 62 liters per minute in accordance with the flow latch outputs 76–80. As a consequence, an air or oxygen flow is delivered to the bellows assembly 14 which corresponds closely (but not exactly) to the flow specified by the setting of the MV and I:E dials 11 and 13. The flow delivered by valves 34–38 is not exactly equal to that specified by the dials 11 and 13 because of the latch count increments of $2^n$ and variations when setting the valve restrictors.

To compensate for the inexactitudes of delivered flow, the tidal volume control circuit of FIG. 6 controls the disabling of the AND gates 86–90 and the duration of the valve acutations so that the flow actually delivered through valves 34–38 more accurately corresponds to the prescribed settings of dials 11, 12 and 13. The circuitry for performing this function comprises tidal volume signal processing and altitude and driving gas correcting means including the D/A converter 39, integrator 40, comparator 103, driving gas correction circuit 104, altitude correction circuit 105, D/A converter 106, latch 58, OR gate 108, comparator 109, integrator 110, and the scaler and multiplier 41.

The D/A converter 39 is a scaling and summing amplifier circuit. Each of the five inputs to converter 39 is preadjusted, or scaled, for example, by resistor scaling so that its signal contribution to the summing amplifier circuit corresponds to actual flow delivered by the related one of the valves 34–38 when actuated and opened such as during calibration testing of the instrument. Thus, an accurate representation of the actual flow delivered by opened ones of the valves 34–38 to the bellows assembly 14 is supplied to inputs of the summing amplifier circuit (not shown) of converter 39. Resultingly, converter 39 generates a flow sum signal on its output 111 as an input to integrator 40. The latter thereupon converts the summed actual flow signal into an indication of volume so that ultimately, as later described, the volume signal on the output 112 of integrator 40 in cooperation with comparator 103 controls the disablement and enablement of AND gates 86–90 over conductor 113 so that the valves 34–38 are appropriately closed and opened for a duration which compensates for inaccuracies between the settings of dials 11 and 13 and the valves 34 and 38 and their related $2^n$ flow control circuitry.

Comparator 103 functions to match the volume indicating signal on the integrator output 112 with a tidal volume related signal which is altitude corrected and air and/or oxygen corrected for controlling the opened-closed duration of valves 34–38 so that the tidal volume of air and/or oxygen delivered to bellows assembly 14 is as required by the settings of the MV, I:E and R dials 11, 12 and 13. The tidal volume required by these settings is as priorly explained: TV=MV/R.

A generation of the tidal volume related signal is initiated by integrating the rate voltage supplied over conductor 75 by the scaler and multiplier 41 in an integrator 110 and furnishing the resultant output voltage over conductor 114 to a first input of the comparator 109. A second input of comparator 109 receives the minute volume voltage from scaler and multiplier 41. When the two input voltages are equal, the rate voltage times delta time=the MV voltage and the delta time is proportional to MV/Rate and is therefore proportional to tidal volume. As a result of input voltage equality, comparator 109 produces an output signal which is passed over conductor 115 through OR gate 108 and conductor 116 for activating latch 58. Upon activating, latch 58 latches and extends the then existent count of counter 55 over its output conductors of cable 117 to the D/A converter 106. The digital number thus present on conductors of cable 117 is proportional to the tidal volume specified by the settings of dials 11, 12 and 13. The number is illustratively between the range of 0 to 512.

The tidal volume count signals on conductor of cable 117 are summed in the D/A converter 106. The summed signal is then applied over conductor 118 to the altitude correction circuit 105 for scaling to adjust the signal levels for altitudes from zero to 6000 feet. The scaling correction is provided because the volume of air which tube restriction permits is a function of the pressure across the tube as well as the density of the air or oxygen through the tube. The regulated supply 27 always supplies air or oxygen at a fixed pressure with respect to atmospheric pressure. The density of the air or oxygen varies with atmospheric pressure.

Illustratively, if the atmospheric pressure is $P_2$, the delivered volume at pressure $P_2=V_2$ and the atmospheric outlet is at a temperature $T_2$ and, resultingly, $P_2V_2/T_2=P_1V_1/T_1$ where $P_1$, $V_1$ and $T_1$ refers to pressure, volume and temperature at the high pressure side. If the temperature $T_1=T_2$, $P_1V_1=P_2V_2$ or $V_2=P_1V_1/P_2$. $P_1=P_2$ delta P, where delta P is maintained by the regulator. Therefore, $V_2=(P_2=$delta $P)V_1/P_2$ and, for variations of $P_2$ (atmosphere), $V_2$ cannot be constant. For small variations of $P_2$, the error would be small without correction. For variations of $P_2$ due to large atmospheric changes, such as would be found at various elevations, the scaling correction (zero to 6000 feet) of the altitude correction circuit 105 is made and the resultant corrected signals are extended over conductor 119 to the driving gas correction circuit 104. The latter comprises an arrangement for manually switching an appropriate scaling device serially between conductors 119 and 120 depending upon whether air or oxygen is driving the valves 34–38.

As a consequence of the foregoing, the signal voltage on conductor 120 accurately represents a prescribed tidal volume signal in accordance with the settings of dials 11, 12 and 13. When the voltages on conductors 120 and 112 are equal, the comparator 103 is activated to disable gates 86–90 and thereby terminate the passage of the binary count signals to valves 34–38. The latter thereupon are deactuated to terminate the inspiration time I and begin the expiration time E. Thus, the inspiration time I is the time required for the integration of the actual flow by integrator 40 to reach the corrected tidal volume related signal from the correction circuit 104. The inspiration time I accordingly is shorter or longer by an amount to compensate for the ± digit counter in the $2^n$ binary number counting by counter 55.

For example, if the 32 liters per minute valve 38 actually delivers 29 liters per minute when opened and the voltage scaling in the D/A converter is set to 29/32 of the value corresponding to the 32 liters per minute valve 38, all of the actuated valves 34–38 would remain actuated for a longer period of time due to the compensating circuit functions to adjust for the 3 liters per minute deficiency. In other words, the actuated valves would be opened long enough to reach the required tidal volume specified by the settings of the dials 11, 12 and 13.

Flow Check Limit Circuitry (FIG. 6)

This circuitry limits the magnitude of the flow through valves 34-38 to 62 liters per minute despite a faulty operation of the latch 56 and whenever the settings of dials 11 and 12 specify a greater flow. An example of such greater flow settings occurs when dials 11 and 12 are set respectively to MV=30 and I:E=3. According to F=MV(1+E/I), the required flow would be 120 liters per minute.

The check circuitry performs the flow limiting functions by controlling the operations of the "OR" gates 81-85 and the "AND" gates 86-90. Effectively, the check circuitry operates all of the "OR" gates 81-85 for causing the actuation of all of the valves 34-38 and to disable the "AND" gates 86-90 when the tidal volume required by settings of dials 11, 12 and 13 is achieved.

A comparator 72 is provided in the check circuitry for controlling the operation of all of the "OR" gates 81-85 whenever the flow voltage produced at the output 70 corresponds to a flow greater than 62 liters per minute. Comparator 72 has a first input 121 connected to a source (not shown) of reference potential which is related to a limiting 62 liters per minute maximum. When the flow voltage is slightly greater than the reference voltage, comparator 72 applies to its output 122 a switching signal which extends through all of the "OR" gates 81-85 and the normally enabled "AND" gates 86-90 for operating all of the valves 34-38 so that the full 62 liters per minute are delivered to the bellows assembly 14.

As priorly explained, the "AND" gates 86-90 are normally enabled to pass a valve actuating signal received from the outputs 91-95 of "OR" gates 81-85. Gates 86-90 are disabled, as already explained, when the tidal volume prescribed by the settings of the dials 11, 12 and 13 has been delivered through valves 34-38 to bellows assembly 14. The disabling of the gates at the 62 liters per minute level has the effect of automatically reducing the I:E ratio from an excessive to a tolerable level when the settings of dials 11 and 12 requires a greater flow. The automatic reduction is achieved by controlling the inspiration time, as priorly described. This time is determined by the time it takes for the corrected tidal volume related signals from the correction circuit 104 to reach the signal level at the output 112 of the integrator 112. The latter signal is an integration of a scaled flow signal corresponding to 62 liters per minute.

Rate-Breaths Per Minute

This circuitry includes a rate voltage integrator 123 and a comparator 125. Its principal function is to regulate the total time for inspiration and expiration. It does so by controlling the total time that the valves 34-38 are opened and closed. The total time corresponds to the rate and illustratively corresponds to breaths per minute. The time interval equals 60 seconds/rate.

An inspiration interval occurs when valves 34-38 are opened to allow the prescribed flow to be delivered to bellows unit 14. The inspiration interval is controllably variable to enable a predetermined tidal volume to be delivered to unit 14 and is then immediately terminated, as priorly explained, to begin the expiration interval. When the latter occurs, valves 34-38 are closed to interrupt the flow to bellows 14. The expiration interval is terminated in accord with the setting of the rate dial 12.

To generate a total time equal to the inspiration and expiration times, the rate voltage supplied to conductor 75 by scaler and multiplier 41 is integrated by integrator 123 until a predetermined voltage is reached. A resultant output of the integrator is applied over conductor 124 to a comparator 125. The output is proportional to the integral from zero to the reference voltage of the rate voltage delta time; the rate voltage times delta time equals the reference voltage; and delta time is proportional to the reference voltage/rate voltage.

Comparator 125 has one input connected to the reference voltage and a second input connected to conductor 124. When the integrated rate voltage on conductor 124 equals the reference voltage, comparator 125 operates to apply a reset signal to its output 127 for resetting, or recycling, the rate integrator 123 and flow integrator 40 and concurrently stepping a sigh counter circuit 126. The expiration interval is thus terminated and another inspiration interval begun. Upon resetting, integrator 102 controls comparator 103 for fully enabling the AND gates 86-90 so that the appropriate valves are again activated and opened as priorly explained. The valves then remain activated and opened until the tidal volume specified by the settings of dials 11, 12 and 13 is achieved.

Tidal Volume Limit

As an adjunct safety precaution to the settings of dials 11, 12 and 13, the tidal volume supplied through valves 34-38 to bellows 14 is limited by a circuit including an integrator 128 and comparator 129. The maximum tidal volume illustratively is between 1.5 and 1.6 liters which, for example, is high enough for adult use.

Integrator 128 operates in synchronism with the rate voltage integrator 110 in the determination of tidal volume. The delta time resulting from minute volume/rate is proportional to the tidal volume. Integrator 128 integrates a reference voltage supplied on conductor 512 and supplies an output on conductor 131. Comparator 129 compares the voltage on conductors 130 and 131 and, when the two are equal, the comparator activates latch 58 via gate 108 to fix, at the latch output, the related tidal volume count existing in counter 55. Illustratively, this corresponds to 1.55 liters.

Sigh Circuit

This circuit 126 of FIG. 6 functions to increase both inspiration and expiration times by fifty percent. It is a counting device which illustratively causes every sixty-fourth breath to adjust voltage levels within comparators 103 and 125 so that the breath is increased to 150% of the required tidal volume and the duration of the exhalation time is also increased to 150% of normal.

Each reset pulse on lead 127 from comparator 125 is counted by sigh circuit 126 until a total of 64 breaths are counted. Circuit 126 then applies control voltages to conductors 132 and 133 so that comparators 125 and 103 are biased to increase the inspiration tidal volume to 150% of normal and the duration of the expiration to 150% of normal.

Clocked Reset

To insure accurate tidal volume and tidal volume limit performance of the control equipment, the circuitry of FIG. 6 is arranged automatically to reset, or recycle, the tidal volume and tidal volume limit integrators 128 and 110 at periodically recurring intervals. The reset is accomplished by a reset signal generated at the binary output 512 of counter 55 each time a count 512 and alternate multiples thereof is achieved in response to counted pulses from clock 54. The reset signal persists as long as the 512 output is activated, that is, for example, from the time the count reaches 512 until the count of 1024. Resultingly, the integrators 110 and 128 and associated comparator circuitry fully recycle during this period and then perform again the functions previously described.

As a consequence, the recycling allows the dials 11, 12 and 13 to be readjusted and the flow control circuitry to respond with the desired flow, tidal volume, and inspiration-expiration ratios.

Cycle Initiate

A manual push-button switch is included in a cycle initiate circuit 139. It activates the comparator 125 for generating an output signal on conductor 127 for resetting the rate and tidal volume integrators 123 and 40 and stepping the sigh counter by one. Circuit 139 permits the push-button to cause an actuation only during the exhalation portion of the cycle. Reset occurs at the instant of switch closure and holding the push-button depressed has no effect on subsequent cycles.

Control circuitry (FIGS. 7-10)

Figure 7:
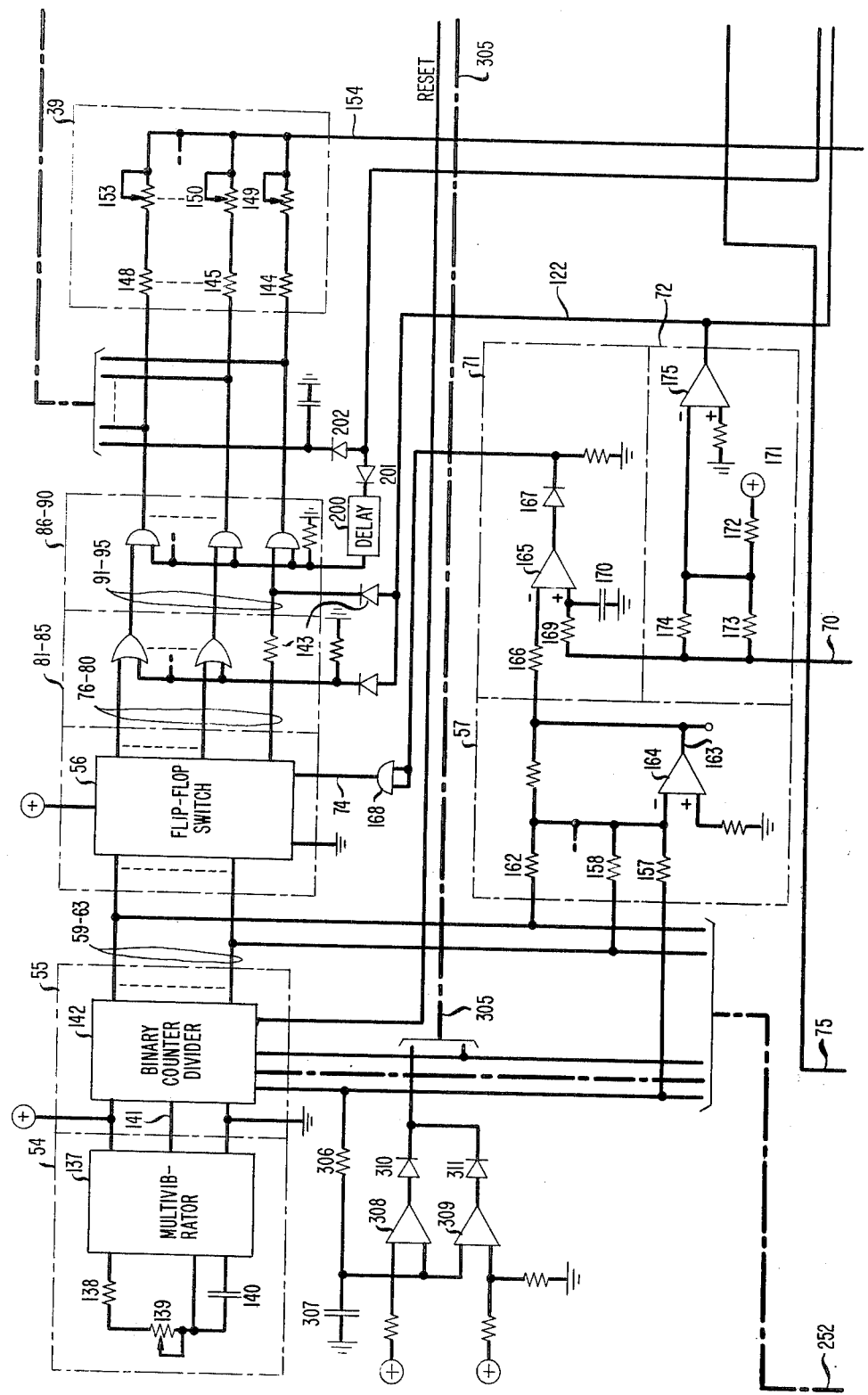
FIGS. 7, 8, 9 and 10 are detailed schematics of the circuits in the flow control equipment.

Clock 54 as shown in FIG. 7 comprises an astable multivibrator 137, the operating frequency of which is controlled by a timing network including resistor 138, potentiometer 139 and capacitor 140. Output pulses on lead 141 drive counter 55.

The latter is a ripple-carry binary counter/divider 142 having twelve outputs $2^{(0)}$ through $2^{(11)}$. These outputs correspond to 1, 2, 4, 8, 16, 32, 64, 128, 256, 512, 1024 and 2048. Outputs 1 through 256 are used for the calculation function which gives 1 to 511 steps. Output 512 is used as a reset for the tidal volume and tidal volume limit integrator circuits. An additional function of the output 256 is to cause the visual and audible alarms to function at a "beep" rate by enabling them if they are actuated.

Latch 56 comprises a flip-flop switching arrangement which receives input signals on leads 59-63 and produces output signals on leads 76-80 in response to a positive pulse on lead 74. The produced output signals are thereafter latched or maintained for the flow delivery functions.

OR gates 81-85 include quad two-input OR gates. The output of each of the quad gates is "ON" if the respective latch flip-flop output on the respective one of the leads 76-80 is "ON". For this function, four of the OR gates and a diode resistor 143 network for the required fifth OR gate are provided.

AND gates 86-90 are formed of quad two-input AND gates arranged to provide five individual AND gates. Functionally, the AND gates are enabled during inspiration periods to pass the outputs of the OR gates 81-85 to activate the five-valve assembly 24 of FIG. 8. The five valves 34-38 of assembly 24 are activated under control of transistor valve drive which respond to the outputs of AND gates 86-90. Valves 34-38 are activated and open during the inspiration time and while the exhalation valve is closed. Conversely, valves 34-38 are closed during exhalation while the exhalation valve is opened.

The air/O$_2$ regulator and supply 26, 27 furnishes the valves with constant air/O$_2$ pressure, for example 38 psi, and operates illustratively from a hospital supply line nominally at 50 psi. Customarily, the regulator includes a filter to remove particulate matter from the input line. A regulator suitable for use with the illustrative embodiment is manufactured by the Norgen Company.

FIG. 7 shows the D/A converter 57 having a plurality of inputs connected via resistors 157-162 to the 1, 2, 4, 8, 16 and 32 outputs of counter 55. Converter 57 is a staircase generator which is responsive to the $2^0$ to $2^5$ counter 55 outputs. The output 163 of the amplifier 164 of converter 57 is a series of voltage steps which increases from zero to a value corresponding to 63 unit steps. Output 163 charges from zero to 63 continuously and generates a cyclically repeating staircase.

The converter output 163 extends the staircase signal to the inverting input of an operational amplifier 165 of comparator 71 via a resistor 166. The noninverting input of amplifier 165 receives from lead 70 via a resistor 169 and capacitor 170 the calculated value of the flow voltage from the front panel dial settings and the scaler and multiplier 41 of FIG. 9. The calculated value of flow has a voltage representative of Flow=MV (1+E/I). When the staircase voltage reaches the value of the flow voltage on lead 70, the output of the comparator amplifier 165 is a rapidly increasing positive voltage which is directed to the flip-flop switch control lead 74 via diode 167 and gate 168 for switching and latching the flip-flop switch 56 so that the binary count of counter 142 output is switched to gates 81-85 and assumes the flow value corresponding to that established by the dials 11-13.

Immediately below comparator 71 in FIG. 7 is the comparator 72 which includes an operational amplifier 175. The latter has its inverting input connected through a resistor network to a reference voltage 171 and to the scaler and multiplier 41 supplied voltage on lead 70. The network includes resistors 172, 173 and 174. When the voltage on lead 70 is greater than the value of the reference voltage (corresponding to the 62 liters per minute), the output of amplifier 175 is directed over lead 122 to the gates 76-80 via diodes 176 and 177 and resistor 178. Resultingly, all five valves 34-38 are activated as priorly explained, via gates 91-95 to insure that a maximum of 62 liters per minute is delivered to a patient whenever the dial settings and scaler and multiplier 41 voltage on lead 70 is for a value greater than 63 liters per minute. The comparator 72 functions in this manner because the staircase voltage from converter 57 is not designed to achieve a value greater than a limit of 63 liters per minute and, accordingly, comparator 71 would not be operated for values greater than 63 liters per minute on lead 70.

Figure 10:
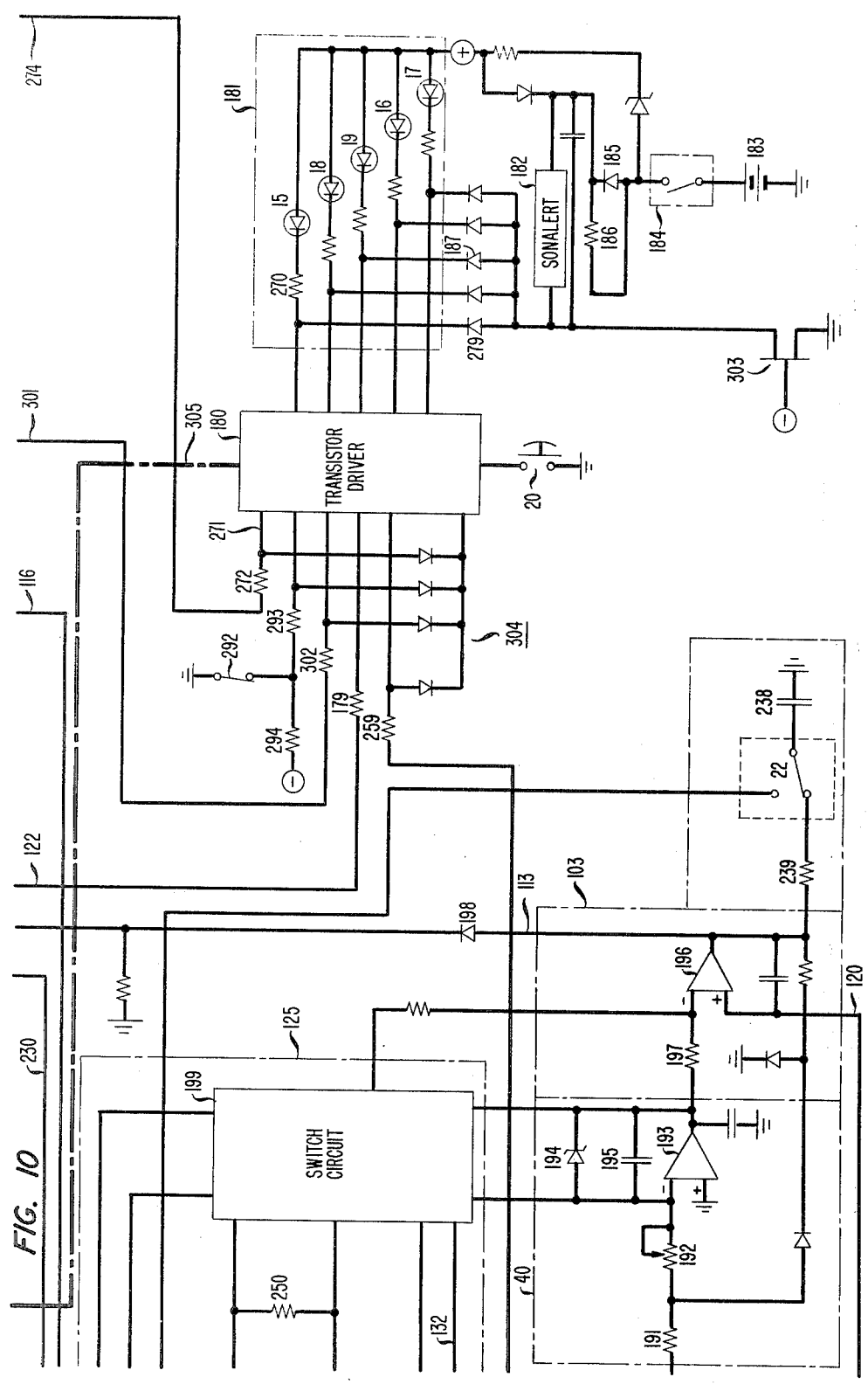

The output signal on lead 122 is also extended through a resistor 179 of FIG. 10 for activating a transistor driver circuit 180 which, in turn, operates an alarm 19 that, on the front panel, indicates that the "Actual I:E Less Than Dial Setting". A Sonalert audible alarm 182 is activated in parallel with alarm 181. These alarms result from the operations of the circuitry of FIGS. 7-10 which automatically alter the I:E when the flow required by the settings of dials 11-13 is greater than 62 liters per minute. Illustratively, from the relationship F=MV(1=E/I), the maximum flow called for at a dial setting of E/I=1:3 is 30(1+3)=120 liters per minute rate which is not delivered by the circuitry of FIGS. 7-10. At an E/I=1:1, the maximum flow is 30(1+1), or 60 liters per minute. As priorly explained, by integrating the actual value of flow (maximum 62 liters per minute) until reaching the prescribed tidal volume, the inspiration time persists for a longer time than indicated by the dial set I:E. For instance, if MV=20 and I:E=3, the flow=20 (1+3)=80 liters per minute and the I:E will automatically be altered to be 1:2.1 which corresponds to 20(1+2.1)=62 liters per minute.

The Sonalert alarm 182 is activated under control of the circuit including a battery 183, a power ON-OFF switch 184, diode 185 and resistor 186 in parallel and diode 187.

Figure 8:
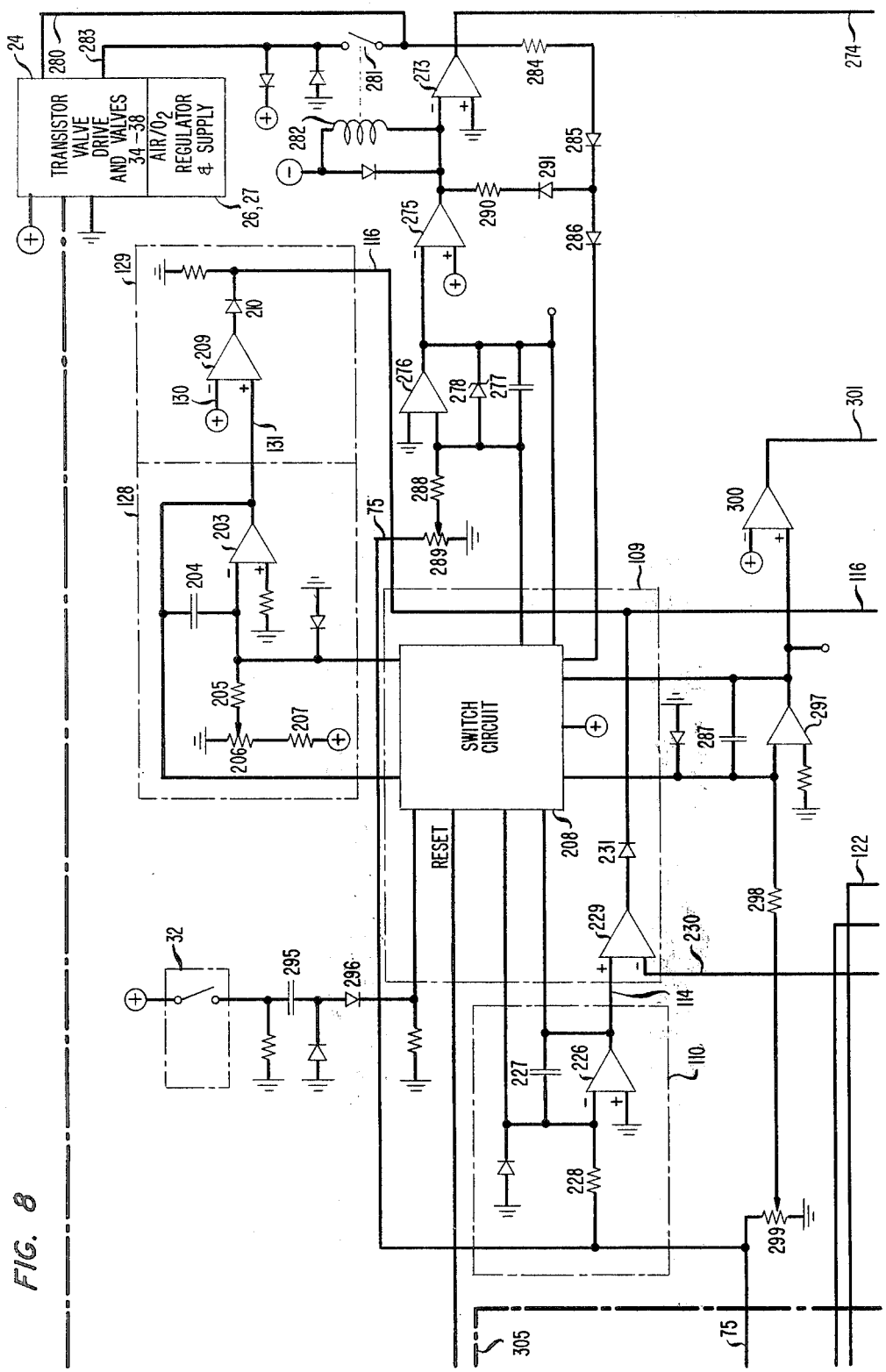

The actual magnitude of the total flow delivered by the "ON" ones of the valves 34-38 is derived by the D/A converter 39 of FIG. 6. As shown in FIGS. 7 and 8, converter 39 is attached to the valve actuating leads 97-101, and includes a network of resistors 144-148 and potentiometers 149-153. The potentiometers are adjacent to enable the summed electrical signal on lead 154 to be at a level which compensates for differences between the desired flow (2, 4 8, 16 and 32 liters per minute) of each valve and the actually closed valve flow. The signal on lead 154 is processed through an inverting operational amplifier 155 to produce an electrical output signal on lead 156, the magnitude of which is representative of the actual valve flow.

Figure 9:
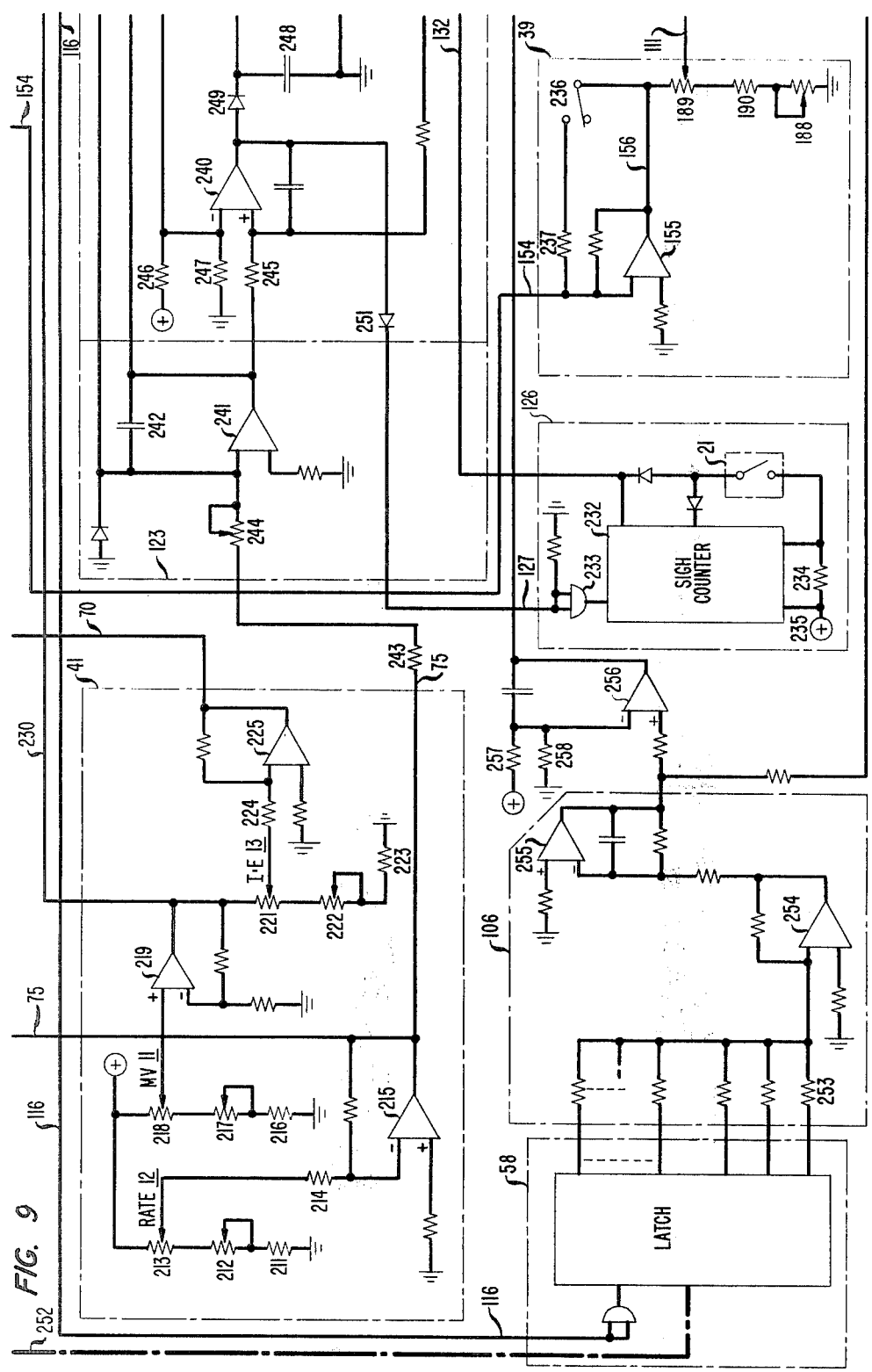

The signal on lead 156 is applied to an altitude scaler network of FIG. 9 including potentiometers 188 and 189 and resistor 190. This scaler network adjusts the operational performance of the equipment in accordance with the altitude location.

An air/oxygen select switch 236 of FIG. 9 is used to change the driving gas scale factor of the D/A converter 39 by inserting a resistor 237 between the inverting input and the output of amplifier 155. The scale factor change is needed to adjust for the effect of the different volume of gas as a result of using air or oxygen. The reason for the difference is the density and viscosity and approximates 5% difference between the two gases. The variation due to resistor 237 changes the gain of amplifier 155.

The altitude and driving gas corrected signal is extended from potentiometer 189 over lead 111 to the flow integrator 40 of FIG. 10 via a resistor 191 and potentiometer 192 to an inverting input of an operational amplifier 193. Potentiometer 192 adjusts the rate of rise of the integrator amplifier 193 output. The integrator starts at the beginning of the rate gate ramp which represents the start of the inspiration cycle. Integrator 40 is reset at the end of the exhalation cycle which is coincident with the end of the rate ramp and under control of comparator 125 as priorly explained. Zener diode 194 functions to limit the voltage across capacitor 195.

The output of amplifier 193 is compared to the calculated and corrected tidal volume signal on lead 120 as priorly explained by comparator 103 of FIG. 10. Comparator 103 includes an operational amplifier 196 which receives the output of amplifier 193 via a resistor 197 at its inverting input and compares it to the tidal volume signal on lead 120 which is received at its noninverting input. When the integrated flow signal reaches the calculated and corrected tidal volume signal, the output of amplifier 196 changes state and this change represents a transition between inspiration and expiration and the output of amplifier 196 is directed via lead 113 and diode 198 to control the disabling of the AND gates 91-95 and deactivation of valves 34-38.

To examine this control further, consider the start of an inspiration. At this time, capacitor 195 has a closed bridging switch from circuit 199 changed to an open such that the output of the amplifier 193 is a logic "0" and the output of amplifier 196 resultingly is positive and is directed to the AND gate 86-90 for causing their enablement via a delay circuit 200 and diode 201 of FIG. 7. Delay circuit 200 is utilized so that the inspiration flow starts after the exhalation valve 29 has fully closed to avoid leakage during closure time. The positive output of amplifier 196 is also directed to the exhalation valve 29 of the valve assembly 24 via diode 202 for insuring that the exhalation valve is closed before the flow signals from valves 34-38 occur.

At the end of inspiration, the output of amplifier 196 changes state to a negative output for causing the AND gate 86-90 rapidly to be disabled to effect a deactivation of activated ones of the valves 34-38. At about the same time, the positive voltage is removed via diode 202 from the control circuit for the exhalation valve 29. The latter remains closed for a short period after the flow through the valves 34-38 is interrupted to allow time for the pressure in the gas lines to decrease so that a small loss does not occur just as the exhalation valve opens proximate to the end of the inhalation interval.

The manual initiation of a breathing cycle is controlled by a front panel pushbutton switch 22, capacitor 238 and a resistor 239 of FIG. 10. Capacitor 238 is charged through resistor 239 to a negative voltage from comparator 103 during the expiration cycle. If switch 22 is actuated, the voltage on capacitor 238 is transferred to an inverting input of an operational amplifier 240 of comparator 125 for effectively causing the rate integration resetting to occur in a shorter time than normal and thus to effect a manual initiation of the breathing cycle. It should be noted that the negative charge on capacitor 238 exists only during exhalation and that during inhalation a positive charge exists on the capacitor 238 and that its transfer to amplifier 240 has no functional effect.

FIG. 9 discloses the scaler and multiplier 41 together with the front panel dials 11, 12 and 13 for generating the minute volume, rate and I:E ratio voltages as well as the voltage corresponding to the flow requirements in liters per minute in accordance with the relationship $F=MV(1+E/I)$.

Consider the Rate circuitry. The front panel dial 12 controlling potentiometer 123 has a range 6 to 40. To achieve it, resistor 211 and potentiometer 212 of FIG. 9 are set so that the voltage at the junction of potentiometer 212 and the dial 12 potentiometer 213 equal 6/40 of the positive voltage and, therefore, that the voltage from the arm of potentiometer 213 is proportional to the Rate from 6 to 40. The arm of potentiometer 213 is connected via a resistor 214 to an inverting input of a multiplier operational amplifier 215 which amplifies the scale voltage and has a negative output that is coupled to the integrators 110 of FIG. 8 and 123 of FIG. 9.

Turning now to minute volume, its range is 2 to 30 and is controlled by the front panel dial 11. To achieve the range, resistor 216 and potentiometer 217 of FIG. 9 are set so that the voltage at the junction of potentiometer 217 and the dial 11 potentiometer 218 equals 2/30 of the positive voltage applied to potentiometer 218 and, therefore, that the voltage from the arm of potentiometer 218 is proportional to the MV from 2 to 30. The latter voltage is applied to the noninverting input of an operational amplifier 219 which multiplies it and provides an output that is extended over lead 230 to both the comparator 109 of FIG. 8 and the I:E circuitry of FIG. 9 including potentiometers 221 and 222 and the resistor 223.

Potentiometer 222 and resistor 223 are selected for the I:E range of 1 to 3 and so that the scaled voltage at the arm of potentiometer 221 is applied via a resistor 224 to an inverting input of an operational amplifier 225 for amplification and for developing a negative output voltage on lead 70 which is proportional to $F = MV(1+E/I)$. The voltage on lead 70 is directed to comparators 71 and 72 as already explained.

The aforementioned rate voltage on lead 75 is processed by two integrators 110 of FIG. 8 and 123 of FIG. 9. The integration by circuit 110 is controlled by an operational amplifier 226 and capacitor 227. The latter is shorted by a switch in circuit 208 during the reset or recycling period under control of the 512 output of the binary counter 55. At all other times, the switch circuit 208 is activated by a logic signal on the 512 output. When it is not shorted upon a transistor from the 512 output, circuit 110 effects an integration of the rate voltage received via a resistor 228 at the inverting input of amplifier 226 for generating an output which is applied to the comparator 109. The latter includes an operational amplifier 229 for comparing the integrated voltage on lead 114 with the minute volume voltage received over lead 230 from amplifier 219. When the integrated voltage is greater than the MV voltage, the output of amplifier 229 becomes sufficiently positive to be directed through diode 231 of OR gate 108 for operating the tidal volume latch 58 of FIG. 9 over lead 116.

Integrator 123 of FIG. 9 comprises an operational amplifier 241 and capacitor 242 for integrating the scaled rate voltage on lead 75. The voltage is extended from lead 75 through resistor 243 and potentiometer 244 to an inverting input of amplifier 241. The integrator generates a ramp the slope of which increases with an increasing rate setting of dial 12. Capacitor 242 is shorted by a switch in circuit 199 during the reset or recycling period of the integrator to "0" under control of the comparator 125 and is open-circuited for the integration.

The ramp voltage at the output of amplifier 241 is direct coupled via a resistor 245 to a noninverting input of the operational amplifier 240 in comparator 125. An inverting input of amplifier 240 is connected to a reference bias voltage derived across resistors 246 and 247.

When the magnitude of the rate ramp exceeds the reference voltage, comparator amplifier 240 provides a positive output for charging capacitor 248 via diode 249 and concurrently activating the switch circuit 199. Upon its activation, switch circuit 199 closes its switches for shorting the capacitors 195 and 242 as priorly explained and thereby effecting their discharge resetting or recycling. Capacitor 248 and resistor 250 serve to hold the switch circuit 199 activated for a long enough period to insure the complete discharge of the capacitors 195 and 242. Upon the discharge of capacitor 248, the switch circuit 199 is deactivated and its shorting switches open to permit the integrator capacitors 195 and 242 to start their cycle again.

The sigh circuit 128 of FIG. 9 comprises a seven-stage binary counter 232 which receives positive drive pulses on lead 127 via a gate 233. The counter is biased in the OFF state by a resistor 234 and voltage 235 and is activated to begin counting pulses when the front panel sigh switch 21 is closed. When the 64th pulse is counted, the $2^6$ output is ON and is coupled via lead 132 to the comparator 125 switching circuit 199 for sigh implementing operations. When the 65th pulse occurs, the $2^0$ and $2^6$ outputs of counter 232 are ON and act to reset the counter via the sigh switch 21.

The output of comparator amplifier 240 is also directed to the drive input of sigh counter 232 via diode 251. Upon counter 232 reaching a count of 64 pulses received via diode 251, a signal is generated at the counter output lead 132 for activating the switch circuit 125 and for effecting a scale factor change in comparators 103 and 125. Resultingly, an increase by 50% is effected in the inhalation and exhalation times as well as the tidal volume for the persistence of the 64th pulse counter state and to effect a sigh function.

Latch 58 of FIG. 9 comprises a flip-flop latch which receives a latch signal on lead 116 from the tidal volume limiting comparator 129 and comparator 109 of FIG. 8 via the OR gate comprised of diodes 210 and 231. Upon receipt of that signal, latch 58 operates and latches so that the binary counter state signals received at its input over cable 252 are extended to its output leads to respective summing resistors 253 of an operational amplifier 254 in the D/A converter 106. The output of the summing amplifier 254 has a value determined by the state of the outputs of latch 58 and the counter 55. Each output of latch 58 contributes to the output of amplifier 254 in accordance with its binary value.

The output of amplifier 254 is applied to the inverting input of a unity gain amplifier 255 and represents the calculated tidal volume signal. The latter is directed to amplifier 196 of comparator 103 and to an amplifier 256 of an alarm comparator. When the calculated tidal volume equals the integrator 40 value, the AND gates 86–90 are disabled to terminate the inspiration interval. When the calculated tidal volume signal exceeds a reference voltage level derived across resistors 257 and 258 for amplifier 256, the transistor driver 180 is activated via resistor 259 to energize a "Setting Exceeds Specifications Visual Alarm 16".

Integrator 128 of FIG. 8 functions, as priorly explained, to limit the tidal volume to 1.5 liters. Circuit 128 includes an operational amplifier 203 and a network including capacitor 204, resistors 205 and 207, and potentiometer 206 for generating a ramp slope corresponding to that of the tidal volume integrator 110. The tidal volume ramp adjustment is controlled by potentiometer 206.

The action of the integrator 128 is now explained with respect to its resetting time which occurs upon the occurrence of the 512th output of the binary counter 55 switching to a logic "1". At that time, a switch in circuit 208 is closed in response to the logic "1" for shorting the capacitor 204. The short is removed when the 512 count switches to a logic "0" and all of the $2^0$ to $2^9$ outputs of counter 55 are "0". As a consequence, both integrators 128 and 110 concurrently initiate tidal volume functions under control of the 512 reset count output and are subsequently reset or recycled upon the occurrence of the logic "1" at that output in cooperation with circuit 208.

The ramp output signal of amplifier 203 appears on lead 131 and is compared against a fixed reference voltage on lead 130 by comparator 129. The comparison is performed by the operational amplifier 209. When the compared signals are equal, the time interval from the start of the ramp of integrator 128 to when the equality occurs corresponds to the interval for a calculated tidal volume calculation of 1.5 liters. The output of amplifier 209 is directed through an OR gate 108 diode 210 over lead 116 for controllably activating latch 58 of FIG. 7 as priorly explained when the output of amplifier 209 is reached corresponding to a limit of 1.5 liters.

As a safety feature in the event of a fault in the transistor valve drive circuitry for the exhalation valve 29 of FIG. 2 and in the valve assembly 24 of FIG. 8, rate voltage integrator and alarm circuits are furnished in FIGS. 8 and 10. These circuits are effective to open the exhalation valve 29 due to the fault and to activate the Ventilate Manually alarm lamp 15 of FIG. 10 which appears on the front panel of the instrument as shown in FIG. 1. Concurrent with the operation of lamp 15, the Sonalert audible alarm 182 of FIG. 10 is operated. Lamp 15 and alarm 182 are activated via resistor 270 and diode 279 under control of the transistor driver of FIG. 10 in response to an alarm signal received on an input 271 via a resistor 272 and lead 274 from a comparator operational amplifier 273 in the alarm circuits of FIG. 8. Amplifier 273 is normally reversed biased in its "off" state during the absence of a fault. Amplifier 273 compares the signal received on its inverting input from another comparator operational amplifier 275. The latter compares an integrator input on its inverting input to a positive reference voltage on its noninverting input. The integrator comprises an operational amplifier 276, capacitor 277 and a Zener diode 278. Capacitor 277 is short circuited during recycling operations by a switch of circuit 208 of FIG. 8 and is open circuited for rate voltage integration during the nonresetting intervals. Circuit 208 is activated in response to two different resetting signals, one of which is from the 512th output of counter 142 of FIG. 7 and another of which is received from the transistor valve drive of valve assembly 24 of FIG. 8. The latter reset signal is extended from assembly 24 via lead 280 and diodes 285 and 286. The activation of circuit 208 of comparator 109 functionally effects the recycling, or discharge, of capacitor 277 of FIG. 8 and for open circuiting the capacitor upon the circuit 208 deactivation for rate voltage integration operations.

The functions of the integrating amplifier 276 and capacitor 277 is essentially to insure that the resetting operation by the transistor valve drive of assembly 24 occurs at the proper time and otherwise to operate the alarms 15 and 182 if it does not.

During the start of an inhalation cycle, which is coincident with the start of an integration by amplifier 276 of the rate voltage supplied to it via resistor 288 and potentiometer 289 from lead 75, the exhalation valve 29 of FIG. 2 is activated and closed under control of a closure from the valve assembly 24 of FIG. 8 through lead 280, a closed contact 281 of relay 282 and lead 283. Relay 282 is operated to effect the closure in reponse to a positive operating voltage supplied from an output of the comparator amplifier 275.

During exhalation, the exhalation valve drive circuits of assembly 24 apply a reset signal to lead 280 indicative of a properly functioning arrangement. The reset signal activates switch circuit 208 of FIG. 8 via resistor 284 and diodes 285 and 286 for effecting the discharge recycling of capacitor 277 as priorly explained for the duration of the exhalation cycle.

In the event that the reset signal does not appear on lead 280, the rate voltage integration by amplifier 276 and capacitor 277 increases at the inverting input of amplifier 275 beyond the reference voltage at the noninverting input of amplifier 275 and resultingly causes its output to switch negatively for effecting a release of relay 282. In releasing, relay 282 opens its contact 281 for inhibiting further closure of the exhalation valve 29. At the same time, the reset pulse is inhibited via resistor 290 and diode 291 and the amplifier 273 is operated to effect the activation of alarms 15 and 182 of FIG. 10 under control of driver 180 as priorly explained.

The Lo Gas Supply Pressure alarm lamp 17 of FIG. 10 which also appears on the front panel of the instrument of FIG. 1 is activated by the transistor driver 180 of FIG. 10 under control of the pressure switch 292 of FIG. 10. The latter is normally open at low pressure of the driving gas. When the pressure exceeds approximately 40 psi, switch 292 closes causing ground to be applied to the junction of resistors 293 and 294 and thus biasing the driver 180 to withhold the alarm activation. Whenever a pressure drop below approximately 35 psi occurs, switch 292 opens and a negative voltage is applied through resistors 293 and 294 for activating driver 180 and, in turn, the alarms 17 and 182.

The Patient Disconnect alarm lamp 18 of FIG. 10 which also appears on the front panel of the instrument of FIG. 1 is activated by the transistor driver 180 of FIG. 10 under control of rate integrator and comparator circuits and a pressure switch 32 of FIGS. 2 and 8. The pressure output of the bellows assembly 14 of FIG. 2 which is supplied to the anesthesia machine is monitored by switch 32 of FIG. 8. Switch 32 is normally opened at low pressure. When actuated by the desired pressure, switch 32 closes to apply a positive reset signal voltage to switch circuit 208 of comparator 109 via a capacitor 295 and diode 296. The positive voltage input to switch 208 exists for a time determined by capacitor 295 and diode 296 and causes switch 208 to effect a discharge recycling of the integrator capacitor 287. After the recycle is completed, capacitor 287 and its associated amplifier 297 generate a ramp voltage in response to an input rate voltage received via resistor 298 and potentiometer 299 from lead 75. When the ramp output voltage of amplifier 297 reaches the reference voltage at the inverting input voltage of comparator operational amplifier 300 of FIG. 8, the latter produces an output on lead 301 for operating the transistor driver 180 of FIG. 10 via resistor 302, and, in turn, activating the alarms 18 and 182 of FIG. 10. Illustratively, the ramp voltage duration is adjusted so that the interval between the closure of switch 32 and the alarm actuation corresponds to approximately two full breaths. It is noteworthy that the reset signal is AC coupled through capacitor 295, that is, that the switch 32 generates a pulse upon closure only and must open and close to generate a next pulse. In the absence of such a reset pulse beyond a duration of illustratively two breaths, the alarms 18 and 182 are operated as already described.

An audible alarm from the Sonalert alarm 182 is provided whenever there is a power loss to the instrument. When power is not interrupted or lost, and power switch 184 is closed, a negative voltage is applied to the gate of the FET transistor 303 for switching it to an "off" state. If the negative voltage is withdrawn, transistor 303 conducts and completes a current path through the audible alarm 182, resistor 186, and switch 184 to battery 183 for signaling a power failure.

A test of all the lamp alarms 15–19 and alarm 182 is conducted by depressing the alarm test button switch 20 of FIG. 10 which also appears on the front panel of the instrument of FIG. 1. The depression closes switch 20 for applying ground to the transistor driver circuit 180 via diodes 304 and thereby activating transistor driver 180 for all of the alarms.

The audible and visual alarms are all pulsating alarms (beep, beep and blink, blink) except for the Actual I:E Less Than Setting (alarm 19). The pulsating effect is achieved at the rate of the 256 count by operating the transistor driver circuit 180 under control of the 256 output of the binary counter 142 of FIG. 7 over cable 305.

An alarm control circuit is shown in FIG. 7 for monitoring the operations of the $2^0$ output of the binary counter 142. The circuit comprises a resistor 306 and capacitor 307 which generate an average of the $2^0$ output which, for example, is 50% of the + voltage applied to counter 142. A pair of comparators 308 and 309 compare the 50% voltage from capacitor 307 to, for example, +3 and +9 volts applied to inputs of the comparators. When the comparator 307 voltage is between 3 and 9 volts, the output of the comparators 308 and 309 is negative and no alarm is given. If the capacitor 307 voltage is below 3 or above 9 volts, the associated comparator output switches positive and is directed via diode 310 and 311 and cable 305 for activating the transistor driver 180 of FIG. 10 and, in turn, all of the visual and audible alarms 15-19 and 182.

The circuit elements suitable for use in the control circuitry of FIGS. 7-10 illustratively are as follows:

| Element | Device | Manu-Facturer | Type |
|---|---|---|---|
| 137 | 4047BPC | Fairchild | COS/MOS low-power monostable/astable multivibrator |
| 142 | F4040BPC | Fairchild | COS/MOS 12-stage ripple-carry binary counter/divider |
| Operational amplifiers such as, 164, 175, 308, 309 | LM324N | National | Low power quad operational amplifier |
| 81-85 | MC14071B | Motorola | quad 2-input "OR" gate |
| 86-90 | F4081BPC | Fairchild | quad 2-input "AND" gate |
| 232 | F4024BPC | Fairchild | 7-stage ripple counter |
| 56 transistor valve drive 24 and transistor drive 180 | MM74C174 ULN 2004A | National Sprague | Hex D filp-flop |
| 199, 208 | MC14066B | Motorola | quadanalog switch quad multiplexer high voltage, high current, Darlington array |

What is claimed is:

1. Equipment for controlling a flow of fluid during inspiration from a source to a utilization means and comprising a plurality of valves adapted to be connected in a parallel arrangement between said source and said utilization means, each of said valves being individually operable to deliver a prescribed fluid flow from said source to said utilization means during inspiration, control means including a first control device independently settable for supplying a distinct minute volume (MV) signal, a second control device independently settable for supplying a distinct breath rate (R) signal and a third control device independently settable for supplying an inspiratory (I) time to expiratory (E) time ratio signal, and circuit means for delivering a predetermined tidal volume (TV) of said fluid from said source to said utilization means and being responsive to a receipt of said minute volume (MV), breath rate (R) and inspiratory (I) time to expiratory (E) time ratio signals for electrically combining said signals in accordance with the function,

MV (1+E/I)

where MV=TV×R and for controlling the operation of said valves to provide said prescribed inspiratory fluid flow and deliver said predetermined tidal volume, and said circuit means comprising means responsive to said minute volume and inspiration to expiration ratio signals for generating a signal prescribing said fluid flow and means responsive to said prescribing signal for operating predetermined ones of said valves to deliver the prescribed fluid flow, and each of the operated ones of said valves delivering a different magnitude of flow from said source to said utilization means.

2. Flow control equipment for automatically regulating the delivery of predetermined tidal volumes of fluid from a source to a utilization means comprising a plurality of valves adapted to be connected in a parallel arrangement between said source and said utilization means, each of said valves being individually operable to deliver a prescribed fluid flow from said source to said utilization means during inspiration, control means including a first control device independently settable for supplying a distinct minute volume (MV) signal, a second control device independently settable for supplying a distinct breath rate (R) signal and a third control device independently settable for supplying an inspiratory (I) time to expiratory (E) time ratio signal, circuit means for delivering a predetermined tidal volume (TV) of said fluid from said source to said utilization means and being responsive to a receipt of said minute volume (MV), breath rate (R) and inspiratory (I) time to expiratory (E) time ratio signals for electrically combining said signals in accordance with the function,

MV (1+E/I)

where MV=TV×R and for controlling the operation of said valves to provide said prescribed inspiratory fluid flow and deliver said predetermined tidal volume, a tidal volume compensation circuit cooperating with said valves for altering said inspiratory fluid flow to compensate for deviations from said predetermined tidal volume set by said control means and including means cooperating with said circuit means for providing a first signal indicative of the actual inspiratory fluid flow from said source to said utilization means and means cooperating with said control means and responsive to said minute volume (MV) signal and breath rate (R) signal for providing a second signal indicative of a calculated tidal volume (TV) equal to MV/R, and a comparator means for comparing said first and second signals and for controlling said valves to compensate for deviations between said first and second signals.

3. The invention of claim 2 wherein said circuit means comprises a flow circuit responsive to a receipt of flow signals generated by said first and third control devices for operating said valves to determine the magnitude of the flow delivered during inspiration and a tidal volume circuit cooperating with said flow circuit and responsive to a receipt of minute volume and rate voltage signals generated by said first and second control devices for controlling the operated time of said valves so that a predetermined tidal volume of said fluid is delivered from said source to said utilization means during inspiration.

4. The invention of claim 3 wherein said tidal volume circuit comprses
   a breath rate circuit responsive to said rate voltage signals for establishing inhalation and exhalation times of said fluid delivery from said source through operated ones of said valves to said utilization means.

5. The invention of claim 3 wherein each of the operated ones of said valves delivers a different binary valued magnitude of fluid flow from said source to said utilization means.

6. The invention of claim 3 wherein said circuit means further comprises a scaler and multiplier including operational amplifier and resistive networks for generating said fluid flow voltage, minute volume voltage and rate voltage signals.

7. The invention of claim 3 wherein said circuit means further comprises a clock and counter arrangement for controlling operations of said flow and tidal volume circuits.

8. The invention of claim 7 wherein
   said counter arrangement includes a binary counter driven to a plurality of count states by signals from said clock, and
   said flow circuit comprises a fluid flow latch operable for maintaining at an output thereof signals indicative of the count state of said binary counter.

9. The invention of claim 8 wherein said flow circuit further comprises
   a converter circuit responsive to output signals indicative of said count state of said binary counter for generating an output flow signal, and
   a flow comparator responsive to a receipt of said output flow signal and to said flow voltage signal for operating said fluid flow latch for maintaining at an output thereof binary valve activating signals indicative of the binary count state of said binary counter upon said fluid flow latch operating.

10. The invention of claim 9 wherein
    said flow circuit further comprises means activatable for gating said binary valve actuating signals to effect the operation of said valves, and
    said tidal volume circuit comprises gate control means for activating said gating means during an inhalation interval and for deactivating said gating means during an exhalation interval.

11. The invention of claim 10 wherein
    said gating means comprises a plurality of OR gates and a plurality of AND gates,
    said OR gates being effective for gating said binary valve actuating signals to said AND gates, and
    said gate control means activates said AND gates to gate said binary valve control signals to said valves for effecting the operation of said valves during said inhalation interval and a release of said valves during said exhalation interval.

12. The invention of claim 11 further comprising
    a flow limiting means responsive to said flow voltage signals for generating flow limit valve actuating signals when the flow required by the settings of the minute volume and inspiration to expiration controls exceed the flow limit, and
    wherein said OR gates said flow limit valve actuating signals to said AND gates and
    said AND gates are activated under control of said gate control means to gate said last-mentioned signals to said valves.

13. The invention of claim 12 wherein said flow limiting means comprises a comparator circuit for comparing said flow voltage signals to a reference voltage corresponding to a predetermined flow limit and for generating flow limit valve actuating signals for concurrently activating all of said valves.

14. The invention of claim 13 further comprising means responsive to said flow limit valve actuating signals for generating an alarm indicating that the actual inspiration to expiration ratio is less than the setting of the inspiration to expiration ratio control.

15. The invention of claim 14 wherein said calculated tidal volume signal producing means includes
    means for integrating said rate voltage signal,
    means for comparing the integrated rate voltage signal and said minute volume voltage signal to provide an output control signal when the compared signals are equal,
    latch circuit controlled by said binary counter and operated by said output control signal for maintaining at an output of said latch means a tidal volume count signal corresponding to the binary count state upon the operation of said latch circuit,
    and means responsive to said tidal volume count signal for providing said calculated tidal volume signal.

16. The invention of claim 15 further comprising
    means cooperating with said binary counter for controlling said latch circuit for limiting the magnitude of the tidal volume of said fluid delivered through said operated ones of said valves from said source to said utilization means.

17. The invention of claim 16 wherein said tidal volume limiting means comprises an integrator and comparator circuit arrangement for providing another output control signal for operating said latch circuit to generate said tidal volume count signal.

18. The invention of claim 14 wherein said fluid flow is delivered from said source through operated ones of said valves to said utilization means during said inhalation interval and is interrupted during said exhalation interval when said valves are released, and
    said tidal volume circuit further comprises
    circuitry responsive to said rate voltage signal for controlling said gate control means for terminating said exhalation interval and initiating said inhalation interval,
    said inhalation interval being terminated by said reference and calculated tidal volume signals comparing circuitry.

19. The invention of claim 18 wherein said controlling circuitry includes
    apparatus for integrating said rate voltage,
    means comparing the integrated rate voltage from said integrating apparatus with a reference voltage for providing an output control signal to control a termination of said exhalation interval and an initiation of said inhalation interval, and means responsive to said last-mentioned signal for resetting said integrating apparatus and said means for integrating said actual flow signal indication.

20. The invention of claim 19 further comprising a sigh circuit operable at prescribed intervals for controlling said tidal volume circuit to increase by prescribed magnitudes said exhalation interval and said predetermined tidal volume of said fluid delivered from said source through said operated ones of said valves to said utilization means.

21. The invention of claim 20 wherein said sigh circuit comprises a multistage binary counter operated in response to each said output control signal from said comparing means for counting to a predetermined number and then controlling said gate control means to effect said increase of said tidal volume and exhalation interval.

22. The invention of claim 14 further comprising means responsive to a cyclically reoccurring count signal from said binary counter for controlling a resetting of said tidal volume circuit.

23. The invention of claim 14 further comprising an exhalation valve means which is deactivated to expel fluid during an exhalation interval and activated during an inhalation interval, and means for monitoring the activation and deactivation of said exhalation valve means to interrupt the actuation of said exhalation valve means in response to a malfunction signal.

24. The invention of claim 23 wherein said monitoring means comprises a circuit operable for integrating said rate voltage signals to generate an output ramp signal, means for resetting the operated integrating circuit in response to a deactivation of said exhalation valve means, means activated by said output ramp signal in the absence of a deactivation of said exhalation valve means within a predetermined period for interrupting further activation of said exhalation valve means, and means operated by said interrupting means for providing an alarm indication.

25. The invention of claim 24 wherein said interrupting means comprises an operational amplifier and an electromechanical relay.

26. The invention of claim 10 wherein said tidal volume compensation circuit comprises means responsive to said valve actuating signals for producing said first signal as a reference tidal volume signal, said tidal volume circuit further comprises means controlled by generated minute volume and rate voltage signals for cooperating with said second signal providing means for producing a calculated tidal volume signal, and said comparator means comprises circuitry for comparing said reference and calculated tidal volume signals to activate said AND gates to gate said valve actuating signals to said valves during an inhalation interval and to deactivate said AND gates to interrupt the gating of said valve activating signals to said valves during an exhalation interval.

27. The invention of claim 26 wherein said reference tidal volume signal producing means comprises means responsive to a receipt of said valve activating signals for translating said last-mentioned signals into a signal indication of the actual flow delivered by the activated ones of said valves from said source to said utilization means, and means for integrating said actual flow signal indication to provide a reference tidal volume signal.

28. The invention of claim 27 wherein said translating means comprises adjustable means compensating for characteristics of said fluid and the altitude at which said equipment is located.

29. The invention of claim 2 further comprising a disconnect alarm circuit including a switch for monitoring the pressure of said fluid delivered from said source to said utilization means, and apparatus responsive to a prolonged deactivation of said monitoring switch in response to a prescribed low pressure for generating an alarm.

30. The invention of claim 29 wherein said generating apparatus comprises an integrator responsive to rate voltage signals for producing a ramp signal, and means controlled by an activation of said monitoring switch in response to a predetermined pressure of said fluid for resetting said integrator to interrupt the producing of said ramp signal.

* * * * *